United States Patent [19]

Brooks et al.

[11] Patent Number: 5,420,282

[45] Date of Patent: May 30, 1995

[54] THIOPYRANO(2,3,4-C,D) INDOLYLOXIME ETHER ALKYLCARBOXYLATES

[75] Inventors: Dee W. Brooks; Pramila Bhatia, both of Libertyville, Ill.

[73] Assignee: Abbott Laboratories, Abbott Park, Ill.

[21] Appl. No.: 197,422

[22] Filed: Feb. 15, 1994

[51] Int. Cl.$^6$ ............... C07D 495/08; A61K 31/47; A61K 31/44
[52] U.S. Cl. ..................... 546/174; 546/270
[58] Field of Search ............ 546/174, 270; 514/338, 514/314

Primary Examiner—David B. Springer
Attorney, Agent, or Firm—Jerry F. Janssen

[57] ABSTRACT

Compounds of the structure

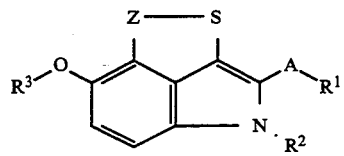

wherein $R^1$ is selected from the group consisting of

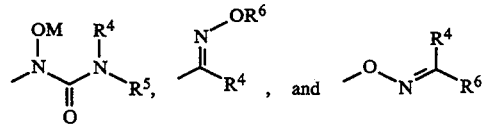

are potent inhibitors of lipoxygenase enzymes and thus inhibit the biosynthesis of leukotrienes. These compounds are useful in the treatment or amelioration of allergic and inflammatory disease states.

5 Claims, No Drawings

THIOPYRANO(2,3,4-C,D) INDOLYLOXIME ETHER ALKYLCARBOXYLATES

TECHNICAL FIELD

This invention relates to compounds having biological activity to inhibit leukotriene biosynthe ted enzyme in the pathway leading to the is biosynthesis of leukotrienes (Samuelsson, B. Leukotrienes: Mediators of Immediate Hypersensitivity Reactions and Inflammation. Science, 120: 568, 1983; Hammarstrom, S. Leukotrienes. Annual Review of Biochemistry, 52: 355, 1983). This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis, cis-1,4-pentadiene structures, converting them to 1-hydroperoxy-trans, cis-2,4-pentadienes. Arachidonic acid, the 5-lipoxygenase substrate which leads to as leukotriene products, is found in very low concentrations in mammalian cells and must first be hydrolyzed from membrane phospholipids through the actions of phospholipases in response to extracellular stimuli. The initial product of 5lipoxygenase action on arachidonate is 5-HPETE which can be reduced to 5-HETE or converted to LTA4. This reactive leukotriene intermediate is enzymafically hydrated to LTB4 or conjugated to the tripeptide glutathione to produce LTC4. LTA4 can also be hydrolyzed nonenzymatically to form two isomers of LTB4. Successive proteolytic cleavage steps convert LTC4 to LTD4 and LTE4. Other products resulting from further oxygenation steps have also been described.

Products of the 5-lipoxygenase cascade are extremely potent substances as which produce a wide variety of biological effects, often in the nanomolar to picomolar concentration range. (Sirois, P. Pharmacology of the Leukotrienes. Advances in Lipid Research. R. Paoletti, D. Kritchevesky, editors, Academic Press, 21: 79, 1985.)

Leukotrienes have been reported to be important mediators in several disease states including: Asthma, Allergic Rhinitis, Rheumatoid Arthritis, Gout, Psoriasis, Adult Respiratory Distress Syndrome, Inflammatory Bowel Disease, Endotoxin Shock, Ischemia-induced Myocardial Injury, Central Nervous Pathophysiology, and Atherosclerosis The enzyme 5-lipoxygenase catalyzes the first step leading to the biosynthesis of all the leukowienes and therefore inhibition of this enzyme provides an approach to limit the effects of all the products of this pathway. Agents capable of abrogating the effects of these potent mediators of pathophysiological processes represent a promising class of therapeutic agents (Brooks, D. W., Bell, R. L., and Carter, G. W. Chapter 8. Pulmonary and Antiallergy Agents, *Annual Reports in Medicinal Chemistry*, Allen, R. C. ed., Academic Press 1988.

SUMMARY OF THE INVENTION

In its principle embodiment, the present invention provides certain substituted thiopyranoindolyloxime derivatives which exhibit activity as inhibitors of leukotriene biosynthesis and are useful in the treatment of allergic and inflammatory disease states in which leukotrienes play a role including asthma, allergic rhinitis, rheumatoid arthritis and gout, psoriasis, adult respiratory distress syndrome, inflammatory bowel disease, endotoxin shock syndrome, ischemia induced myocardial injury, atherosclerosis, and central nervous system pathology resulting from the formation of leukotrienes following stroke or subarachnoid hemorrhage.

The present invention provides a compound of the formula

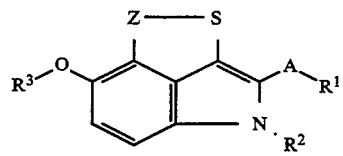

or a pharmaceutcially acceptable salt thereof where A is selected from straight or branched alkylene of one to twelve carbon atoms, cycloalkylene of three to eight carbon atoms, and alkoxyalkylene in which the alkyoxy and alkylene portions are independently of one to six carbon atoms.

In the compounds of the present invention, $R^1$ is selected from the group consisting of

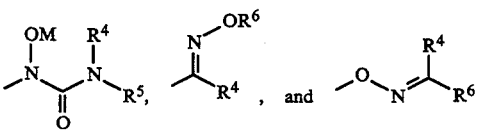

where M is a pharmaceutically acceptable cation or a metabolically cleavable group, $R^4$ and $R^5$ are independently selected from hydrogen, alkyl of one to six carbon atoms, hydroxyalkyl in which the alkyl portion is of one to six carbon atoms, alkoxyalkyl in which the alkoxy and alkyl portions are independently of one to six carbon atoms, (alkoxyalkoxy)alkyl in which the alkoxy and alkyl portions are independently of one to six carbon atoms, carboxyalkyl in which the alkyl portion is of one to six carbon atoms, phenylalkyl in which the alkyl portion is of one to six carbon atoms, and phenoxyalkyl in which the alkyl portion is of one to six carbon atoms; and R6 is selected from hydrogen, alkyl of one to six carbon atoms, hydroxyalkyl of one to six carbon atoms, carboxyalkyl in which the alkyl portion is of one to six carbon atoms, (C-malanato)alkyl in which the alkyl portion is of one to six carbon atoms, (N-alkyl-N-hydroxylaminocarbonyl)alkyl in which the two alkyl portions are independently of one to six carbon atoms, (alkoxycarbonyl)alkyl in which the alkoxy and alkyl portions are independently of one to six carbon atoms, alkanoyl of one to six carbon atoms, (aminocarbonyl)alkyl in which the alkyl portion is of one to six carbon atoms, (alkylaminocarbonyl)alkyl in which the alkyl portions are independently of one to six carbon atoms, (dialkylaminocarbonyl)alkyl in which the alkyl portions are independently of one to six carbon atoms, (N-morpholinocarbonyl)alkyl in which the alkyl portion is of one to six carbon atoms, and tetrazolylalkyl in which the alkyl portion is of one to six carbon atoms.

In the structural formula shown above, $R^2$ is selected from phenylalkyl in which the alkyl portion is of one to six carbon atoms, and heteroarylalkyl in which the alkyl portion is of one to six carbon atoms, and the heteroaryl portion is selected from pyridyl, thienyl, furyl, indolyl, pyrazinyl, isoquinolyl, quinolyl, imidazolyl, pyrimidyl, benzo[b]furyl, benzo[b]thienyl, thiazolyl, benzothiazolyl, and carbazolyl. The phenyl or heteroaryl group may be substituted with up to three substituents selected from (1) alkyl of one to six carbon atoms, (2) haloalkyl of one to six carbon atoms, (3) alkoxy of one to six carbon atoms, (4) hydroxy, (5) halogen, (6) pyridyl, optionally substituted with alkyl of one to six carbon atoms, haloalkyl of one to six carbon atoms, alkoxy of one to six carbon atoms, hydroxy, or halogen, and (6) pyridyloxy, optionally substituted with alkyl of one to six carbon atoms, haloalkyl of one to six carbon atoms, alkoxy of one to six carbon atoms, hydroxy, or halogen.

$R^3$ is selected from the group consisting of (a) alkyl of one to six carbon atoms, (b) alkoxy of one to six carbon atoms, (c) unsubstituted phenyl, (d) substituted phenyl, (e) unsubstituted phenoxy, (f) substituted phenoxy, (g) unsubstituted or substituted phenylalkyl wherein the alkyl portion is of one to six carbon atoms, (h) unsubstituted or substituted phenylalkoxy wherein the alkoxy portion is of one to six carbon atoms, (i) unsubstituted naphthyl, (j) substituted naphthyl, (k) unsubstituted naphthyloxy, (l) substituted naphthyloxy, (m) unsubstituted or substituted naphthylalkyl wherein the alkyl portion is of one to six carbon atoms, and (n) unsubstituted or substituted naphthylalkoxy wherein the alkoxy portion is of one to six carbon atoms. In items (d), (f), (g), (h), (j), (l), (m), and (n), the rings, when substituted, are substituted with a substituent selected from the group consisting of (1) alkyl of one to six carbon atoms, (2) alkoxy of one to six carbon atoms, (3) haloalkyl of one to six carbon atoms, (4) halogen, (5) unsubstituted phenyl, (6) phenyl substituted with a substituent selected from the group consisting of alkyl of one to six carbon atoms, alkoxy of one to six carbon atoms, haloalkyl of one to six carbon atoms, and halogen, (7) unsubstituted pyridyl, (8) pyridyl substituted with a substituent selected from the group consisting of alkyl of one to six carbon atoms, alkoxy of one to six carbon atoms, haloalkyl of one to six carbon atoms, and halogen, (9) unsubstituented thienyl, (10) thienyl substituted with a substituent selected from the group consisting of alkyl of one to six carbon atoms, alkoxy of one to six carbon atoms, haloalkyl of one to six carbon atoms, and halogen, (11) unsubstituted furyl, (12) furyl substituted with a substituent selected from the group consisting of alkyl of one to six carbon atoms, alkoxy of one to six carbon atoms, haloalkyl of one to six carbon atoms, and halogen, (13) unsubstituted benzo(b)thienyl, (14) benzo(b)thienyl substituted with a substituent selected from the group consisting of alkyl of one to six carbon atoms, alkoxy of one to six carbon atoms, haloalkyl of one to six carbon atoms, and halogen, (15) unsubstituted benzo(b)furyl, (16) benzo(b)furyl substituted with a substituent selected from the group consisting of alkyl of one to six carbon atoms, alkoxy of one to six carbon atoms, haloalkyl of one to six carbon atoms, and halogen, (17) as unsubstituted thiazolyl, and (18) thiazolyl substituted with a substituent selected from the group consisting of alkyl of one to six carbon atoms, alkoxy of one to six carbon atoms, haloalkyl of one to six carbon atoms, and halogen; (17) unsubstituted thiazolyl, and (18) thiazolyl substitueted with a substituent selected from the group consisting of alkyl of one to six carbon atoms, alkoxy of one to six carbon atoms, haloalkyl of one to six carbon atoms, and halogen.

In addition to the substituent groups indicated as (a) through (n) above, $R^3$ is also selected from (o) unsubstituted pyridyl, (p) substituted pyridyl, (q) unsubstitueted pyrazinyl, (r) substituted pyrazinyl, (s) unsubstituted quinolyl, (t) substituted quinolyl, (u) unsubstituted isoquinolyl, (v) substituted isoquinolyl, (w) unsubstituted imidazolyl, (x) substituted imidazolyl, (y) unsubstituted indolyl, (z) substituted indolyl, (aa) unsubstituted quinazolinyl, (bb) substituted quinazolinyl, (cc) unsubstituted pyrrolyl, (dd) substituted pyrrolyl, (ee) unsubstituted pyrimidinyl, (ff) substituted pyrimidinyl, (gg) unsubstituted thiazolyl, (hh) substituted thiazolyl, (ii) unsubstituted benzothiazolyl, (jj) substituted benzothiazolyl, (kk) unsubstituted oxazolyl, and (ll) substituted oxazolyl. In substituted groups (p), (r), (t), (v), (x), (z), (bb), (dd), (ff), (hh), (jj), and (ll), the substituents groupos are selected from the group consisting of (1) alkyl of one to six carbon atoms, (2) alkoxy of one to six carbon atoms, (3) haloalkyl of one to six carbon atoms, (4) halogen, (5) unsubstituted phenyl, and (6) phenyl substituted with a substituent selected from the group consisting of alkyl of one to six carbon atoms, alkoxy of one to six carbon atoms, and halogen.

The group Z is selected from the group consisting of alkylene of one to four carbon atoms and alkenylene of one to four carbon atoms. That is, Z, together with the sulfur and carbon atoms to which it is attached, form a ring of 5- to 8-members, fused to the indole nucleus.

In another embodiment, the present invention provides pharmaceutical compositions which comprise a therapeutically effective amount of compound as defined above in combination with a pharmaceutically acceptable carrier.

In yet another embodiment, the present invention provides a method of inhibiting leukotriene biosynthesis in a host mammal in need of such treatment comprising administering to a mammal in need of such treatment a therapeutically effective amount of a compound as defined above.

DETAILED DESCRIPTION

As used throughout this specification and the appended claims, the following terms have the meanings specified.

The term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "alkylene" denotes a divalent group derived from a saturated hydrocarbon by the removel of two hydrogen atoms. Examples of alkylene are —$CH_2$—, —$CH_2CH_2$—, and the like.

The term "alkylamino" refers to a group having the structure —NHR' wherein R' is alkyl, as previously defined, Examples of alkylamino include methylamino, ethylamino, iso-propylamino and the like.

The term "dialkylamino" refers to a group having the structure —NR'R'' wherein R' and R'' are alkyl, as previously defined. Examples of dialkylamino include, dimethylamino, diethylaminocarbonyl, methylethylamino, and the like.

The term "aminocarbonyl" represent an amide group; i.e. an amino group attached to the parent molecular moiety through a carbonyl group.

The term "alkylaminocarbonyl" refers to an alkylamino group, as previously defined, attached to the parent molecular moiety through a carbonyl group. Examples of alkylaminocarbonyl include methylaminocarbonyl, ethylaminocarbonyl, isopropylaminocarbonyl and the like.

The term "dialkylaminocarbonyl" refers to a dialkylamino group, as definded above, attached to the parent molecular moiety through an alkylene group. Examples of dialkylaminocarbonyl groups include N,N-dimethylaminocarbonyl, N,N-diethylaminocarbonyl, N,N-diisopropylaminocarbonyl and the like.

The term "(aminocarbonyl)alkyl" refers to an aminocarbonyl group, as defined above, attached to the parent molecular moiety through an alkylene group. Examples of (aminocarbonyl)alkyl groups include acetamido, propionamido, and the like.

The term "(alkylaminocarbonyl)alkyl" refers to an alkylaminocarbonyl group, as defined above, attached to the parent molecular moiety through an alkylene group. Examples of (alkylaminocarbonyl)alkyl groups include N-methylacetamido, N-ethylacetamido, N-isopropylacetamido, N-methylpropionamido, and the like.

The term "(dialkylaminocarbonyl)alkyl" refers to a dialkylaminocarbonyl group, as defined above, attached to the parent molecular moiety through an alkylene group. Examples of (dialkylaminocarbonyl)alkyl groups include N,N-dimethylacetamido, N,N-dimethylacetamido, N,N-dimethylpropionamido, and the like.

The term "alkylthio" refers to an alkyl group, as defined above, attached to the parent molecular moiety through a sulfur atom and includes such examples as methylthio, ethylthio, propylthio, n-, sec- and tert-butylthio and the like.

The term "alkanoyl" represents an alkyl group, as defined above, attached to the parent molecular moiety through a carbonyl group. Alkanoyl groups are exemplified by formyl, acetyl, propionyl, butanoyl and the like.

The term "alkanoylamino" refers to an alkanoyl group, as previously defined, attached to the parent molecular moiety through a nitrogen atom. Examples of alkanoylamino include formamido, acetamido, and the like.

The term "N-alkanoyl-N-alkylamino" refers to an alkanoyl group, as previously defined, attached to the parent molecular moiety through an aminoalkyl group. Examples of N-alkanoyl-N-alkylamino include N-methylformamido, Nmethylacetamido, and the like.

The terms "alkoxy" or "alkoxyl" denote an alkyl group, as defined above, attached to the parent molecular moiety through an oxygen atom. Representative alkoxy groups include methoxyl, ethoxyl, propoxyl, butoxyl, and the like.

The term "alkoxyalkoxyl" refers to an alkyl group, as defined above, attached through an oxygen to an alkyl group, as defined above, attached in turn through an oxygen to the parent molecular moiety. Examples of alkoxyalkoxyl include methoxymethoxyl, methoxyethyoxyl, ethoxyethoxyl and the like.

The term "(alkoxyalkoxyl)alkyl" as used herein refers to an alkoxyalkoxyl group, as defined above, attached to the parent molecular moiety through an alkylene group. Examples of (alkoxyalkoxyl)alkyl include methoxymethoxymethyl, methoxyethyoxymethyl ethoxyethoxymethyl and the like.

The term "alkoxyalkyl" refers to an alkoxy group, as defined above, attached through an alkylene group to the parent molecular moiety.

The term "carboxyalkyl" refers to a group having the formula —COOB, in which B is hydrogen, a pharmaceutically acceptable salt or a metabolically cleavable group, attached to the parent molecular moiety through an alkylene group. as Representative carboxyalkyl groups include 1-carboxyethyl, 2-carboxyethyl, 1-carboxypropyl, and the like.

The term "alkoxycarbonyl" represents an ester group; i.e. an alkoxy group, attached to the parent molecular moiety through a carbonyl group such as methoxycarbonyl, ethoxycarbonyl, and the like. alkoxycarbonylalkyl The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The term "alkenylene" denotes a divalent group derived from a straight or branched chain hydrocarbon containing at least one carbon-carbon double bond. Examples of alkenylene include —CH=CH—, —CH$_2$CH=CH—, —C(CH$_3$)=CH—, —CH$_2$CH=CHCH$_2$—, and the like.

The term "alkynylene" refers to a divalent group derived by the removal of two hydrogen atoms from a straight or branched chain acyclic hydrocarbon group is containing a carbon-carbon triple bond. Examples of alkynylene include —CH≡CH , —CH≡CH—CH$_2$—, —CH≡CH—CH(CH$_3$)—, and the like.

The term "cycloaikyl" denotes a monovalent group derived from a monocyclic or bicyclic saturated carbocyclic ting compound by the removal of a single hydrogen atom. Examples include cyclopropyl, cyclobutyl, cyclopentyl, cyclohexyl, bicyclo[2.2.1]heptanyl, and bicyclo[2.2.2]octanyl.

The term "cycloalkylene" refers to a divalent group derived from a saturated carbocyclic hydrocarbon by the removal of two hydrogen atoms, for example cyclopentylene, cyclohexylene, and the like.

The term "phenylalkyl" refers to a phenyl group, attached to the parent molecular moiety through an alkylene group. Representative (carbocyclic aryl)alkyl groups include phenylmethyl, phenylethyl, phenylpropyl, 1-naphthylmethyl, and the like.

The term "heteroaryl" is used herein to refer to 5- and 6-membered aromatic rings having in the ring one, two, or three heteroatoms selected from N, O, and S, and also including benzo fused analogs of these 5- and 6-membered heterocyclic aromatic rings including, but not limited to pyridyl, quinolyl, furyl, benzofuryl, thienyl, thiazolyl, pyrimidyl, indolyl, and the like.

The term "heteroarylalkyl" refers to a heteroaryl group as defined above, as attached to the parent molecular moiety through an alkylene group. Representative heteroarylalkyl groups include pyrdidylmethyl, theinylmethyl, thienylethyl, furylmethyl, and the like.

The term "haloalkyl" denotes an alkyl group, as defined above, having one, two, or three halogen atoms attached thereto and is exemplified by such groups as chloromethyl, bromoethyl, trifluoromethyl, and the like.

The term "hydroxyalkyl" represents an alkyl group, as defined above, substituted by one to three hydroxyl groups with the proviso that no more than one hydroxy group may be attached to a single carbon atom of the alkyl group.

The term "phenoxy" refers to a phenyl group attached to the parent molecular moiety through an oxygen atom.

phenoxyalkyl

The term "phenylthio" refers to a phenyl group attached to the parent molecular moiety through a sulfur atom.

The term "pyridyloxy" refers to a pyridyl group attached to the parent is molecular moiety through an oxygen atom.

The term "metabolically cleavable group" denotes a group which is cleaved in vivo to yield the parent molecule of the structural formulae indicated above wherein B is hydrogen. Examples of metabolically cleavable groups include —COR, —COOR, —CONRR and —CH$_2$OR radicals where R is selected independently at each occurrence from alkyl, trialkylsilyl, carbocyclic aryl or carbocyclic aryl substituted with one or more of C$_1$–C$_4$ alkyl, halogen, hydroxy or C$_1$–C$_4$ alkoxy. Specific examples of representative metabolically cleavable groups include acetyl, methoxycarbonyl, benzoyl, methoxymethyl and trimethylsilyl groups.

By "pharmaceutically acceptable salt" it is meant those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M Berge, et al. describe pharmaceutically acceptable salts in detail in *J. Pharmaceutical Sciences*, 1977, 66: 1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, as camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pierate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Compounds of the present invention may exhibit stereoisomefism by virtue of the presence of one or more asymmetric or chiral centers in the compounds. The present invention contemplates the various stereoisomers and mixtures thereof. Desired enantiomers are obtained by chiral synthesis from commercially available chiral starting materials by methods well known in the art, or may be obtained from mixtures of the enantiomers by resolution using known techniques.

PREFERRED EMBODIMENTS

Preferred compounds of the present invention axe those having the structure

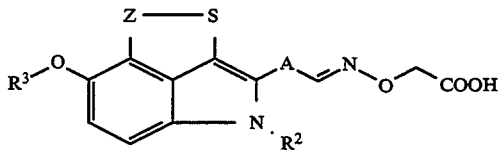

or a pharmaceutically acceptable salt thereof wherein R$^3$, Z, A, and R$^2$, have the values defined above.

Compounds contemplated as falling within the scope of this embodiment include, but are not limited to:

3-[1-(4-chlorobenzyl)-4-methyl-6-(quinolin-2-ylmethoxy)-4,5-dihydro-1H-thiopyrano[2,3,4-c,d]indol-2-yl]-2,2-dimethylpropionaldehyde oxime-O-acetic acid, 3-[1-(4-chlorobenzyl)-4-methyl-6-(5-phenylpyridin-2-ylmethoxy)-4,5-dihydro-1H-thiopyrano[2,3,4-c,d]indol-2-yl]-2,2-dimethylpropionaldehyde oxime-O-acetic acid, 3-[1-(4-chlorobenzyl)-4-methyl-6-(pyrid-2-ylmethoxy)-4,5-dihydro-1H-thiopyrano[2,3,4-c,d]indol-2-yl]-2,2-dimethylpropionaldehyde oxime-O-acetic acid, 3-[1-(4-chlorobenzyl)-4-methyl-6-(thiazo-2-ylmethoxy)-4,5-dihydro-1H-thiopyrano[2,3,4-c,d]indol-2-yl]-2,2-dimethylpropionaldehyde oxime-O-acetic acid, 3-[1-(4-chlorobenzyl)-4-methyl-6-(oxazol-5-ylmethoxy)-4,5-dihydro-1H-thiopyrano[2,3,4-c,d]indol-2-yl]-2,2-dimethylpropionaldehyde oxime-O-acetic acid, 3-[1-(4-chlorobenzyl)-4-methyl-6-(naphth-2-ylmethoxy)-4,5-dihydro-1H-thiopyrano[2,3,4-c,d]indol-2-yl]-2,2-dimethylpropionaldehyde oxime-O-acetic acid, 3-[1-(4-chlorophenyl)-4-methyl-6-(isoquinolin-3-ylmethoxy)-4,5-dihydro-1H-thiopyrano[2,3,4-c,d]indol-2-yl]-2,2-dimethylpropionaldehyde oxime-O-acetic acid, 3-[1-(4-chlorobenzyl)-4-methyl-6-(6-methoxyquinolin-2-ylmethoxy)-4,5-dihydro-1H-thiopyrano[2,3,4-c,d]indol-2-yl]-2,2-dimethylpropionaldehyde oxime-O-acetic acid, 3-[1-(4-chlorobenzyl)-4-methyl-6-((4-chlorophenyl)pyrid-2-ylmethoxy)-4,5-dihydro-1H-thiopyrano[2,3,4-c,d]indol-2-yl]-2,2-dimethylpropionaldehyde oxime-O-acetic acid, 3-[1-(4-chlorobenzyl)-4-methyl-6-(6-chloroquinolin-2-ylmethoxy)-4,5-dihydro-1H-thiopyrano[2,3,4-c,d]indol-2-yl]-2,2-dimethylpropionaldehyde oxime-O-acetic acid, 3-[1-(pyrid-3-ylmethyl)-4-methyl-6-(5-phenylpyridin-2-ylmethoxy)-4,5-dihydro-1H-thiopyrano[2,3,4-c,d]indol-2-yl]-2,2-dimethylpropionaldehyde oxime-O-acetic acid, 3-[1-(4-fluorobenzyl)-4-methyl-6-(quinolin-2-ylmethoxy)-4,5-dihydro-1H-thiopyrano[2,3,4-c,d]indol-2-yl]-2,2-dimethylpropionaldehyde oxime-O-acetic acid, 3-[1-(4-fluorobenzyl)-4-methyl-6-(5-phenylpyridin-2-ylmethoxy)-4,5-dihydro-1H-thiopyrano[2,3,4-c,d]indol-2-yl]-2,2-dimethylpropionaldehyde oxime-O-acetic acid, 3-[1-(4-phenoxyphenylmethyl)-4-methyl-6-(quinolin-2-ylmethoxy)-4,5-dihydro-1H-thiopyrano[2,3,4-c,d]indol-2-yl]-2,2-dimethylpropionaldehyde oxime-O-acetic acid, 3-[1-(4-(4-fluorophenoxy)phenylmethyl)-4-methyl-6-(quinolin-2-ylmethoxy)-4,5-dihydro-1H-thiopyrano[2,3,4-c,d]indol-2-yl]-2,2-dimethylpropionaldehyde oxime-O-acetic acid, 3-[1-(4-(pyrid-2-yl)phenylmethyl)-4-methyl-6-(quinolin-2-ylmethoxy)-4,5-dihydro1H-thiopyrano[2,3,4-c,d]indol-2-yl]-2,2-dimethylpropionaldehyde oxime-O-acetic acid, 3-[1-(4-(pyrid-2-yloxy)phenylmethyl)-4-methyl-6-(quinolin-2-ylmethoxy)-4,5-dihydro-1H-thiopyrano[2,3,4-c,d]indol-2-yl]-2,2-dimethylpropionaldehyde oxime-O-acetic acid,

[1-(4-chlorobenzyl)-4-methyl-6-(quinolin-2-ylmethoxy)-4,5-dihydro-1H-thiopyrano[2,3,4-c,d]indol-2-ylmethoxy]acetaldehyde oxime-O-acetic acid, 3-[1-(4-chlorobenzyl)-4-methyl-6-(quinolin-2-ylmethoxy)-4,5-dihydro-1H-thiopyrano[2,3,4-c,d]indol-2-ylmethoxy]propionaldehyde oxime-O-acetic acid,

[1-(4-chlorobenzyl)-4-methyl-6-(5-phenylpyridin-2-ylmethoxy)-4,5-dihydro-1H-thiopyrano[2,3,4-c,d]indol-2-ylmethoxy]acetaldehyde oxime-O-acetic acid, and 3-[1-(4-chlorobenzyl)-4-methyl-6-(5-phenylpyridin-2-ylmethoxy)-4,5-dihydro-1H-thiopyrano[2,3,4-c,d]indol-2-ylmethoxy]propionaldehyde oxime-O-acetic acid.

Preferred compounds are those in which $R^2$ is optionally substituted phenylalkyl and $R^3$ is optionally substituted pyridylalkyl or quinolylalkyl, where the alkyl portion is of one to six carbon atoms and the optional substituents are selected from (a) alkyl of one to six carbon atoms, (b) alkoxy of one to six carbon atoms, (c) s haloalkyl of one to six carbon atoms, (d) halogen, and (e) phenyl, optionally substituted with alkyl of one to six carbon atoms or halogen.

Particularly preferred compounds are:

3-[1-(4-chlorobenzyl)-4-methyl-6-(quinolin-2-ylmethoxy)-4,5-dihydro-1H-thiopyrano[2,3,4-c,d]indol-2-yl]-2,2-dimethylpropionaldehyde oxime-O-acetic acid, and 3-[1-(4-chlorobenzyl)-4-methyl-6-(5-phenylpyridin-2-ylmethoxy)-4,5-dihydro-1H-thiopyrano[2,3,4-c,d]indol-2-yl]-2,2-dimethylpropionaldehyde oxime-O-acetic acid.

Inhibition of Leukotriene Biosynthesis In Vitro

Inhibition of leukotriene biosynthesis was evaluated in an assay, involving calcium ionophore-induced $LTB_4$ biosynthesis expressed human whole blood. Human heparinized whole blood was proincubated with test compounds or vehicle for 15 min at 37° C. followed by calcium ionophore A23187 challenge (final concentration of 8.3 $\mu M$) and the reaction terminated after 30 minutes by adding two volumes of methanol containing prostaglandin $B_2$ as an internal recovery standard. The methanol extract was analyzed for $LTB_4$ using a commercially available radioimmunoassay.

The compounds of this invention inhibit leukotriene biosynthesis in human whole blood. Representative results for specific examples are: $IC_{50}=2.7$ $\mu M$ for Example 1, and $IC_{50}=0.4$ $\mu M$ for Example 2.

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parentoral injection, or for rectal administration.

The pharmaceutical compositions of this invention can be administered to humans and other animals orally, rectally, parentorally, intracisternally, intravaginally, intraperitoneally, topically (as by powders, ointments, or drops), bucally, or as an oral or nasal spray. The term "parentoral" administration as used herein refers to modes of administration which include intravenous, intramuscular, intraperitoneal, intrasternal, subcutaneous and intraarticular injection and infusion.

Pharmaceutical compositions of this invention for parentoral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as locithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium titrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and as sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonire clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can is be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably as suppositories which can be prepared by mixing the compounds of this invention with suitable non-irritating excipients or carders such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carder and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may as be divided into multiple doses for purposes of administration, e.g. two to four separate doses per day.

Preparation of the Compounds of this Invention

The compounds of this invention may be prepared by a variety of synthetic routes. Representative procedures are outlined in the following Schemes.

A general route to the compounds of this invention is shown in Scheme 1. Indole intermediate 3 is prepared by a Fischer-indole condensation between substituted phenylhydrazine 1, in which $R^2$ is defined above, and carbonyl intermediate 2 in which Q is alkylene or cycloalkylene. Demethylation of indole 3, for example by treatment of a solution of 3 in t-butylthiol with $AlCl_3$ provides hydroxyindole 4 which is alkylated with an optionally substituted allyl bromide in the presence of an inorganic base such as $K_2CO_3$ in an organic solvent (e.g. DMF) to form allyloxyindole intermediate 5 in which $R^8$ and $R^9$ are hydrogen or alkyl of one to four carbon atoms. Heating allyloxyindole 5 and an acid such as p-toluenesulfonic acid in a high boiling organic solvent such as 1,2-dichlorobenzene is results in a Claisen rearrangement followed by cyclization of the intermediate 5-hydroxy-4-allylindole to produce thiopyranoindole 6. Alkylation of 6 with $R_3X$, where $R_3$ is defined above and X is a leaving group such as halogen, tosylate or mesylate, in the presence of an inorganic base such as sodium hydride, lithium diisopropylamine, butyl lithium, sodium hexamethyldisilazide, potassium tertbutoxide, or potassium hydride provides thiopyranoindole 7. Key intermediate 8 is prepared by reduction of ester 7, for example by reaction with sodium borohydride and calcium chloride.

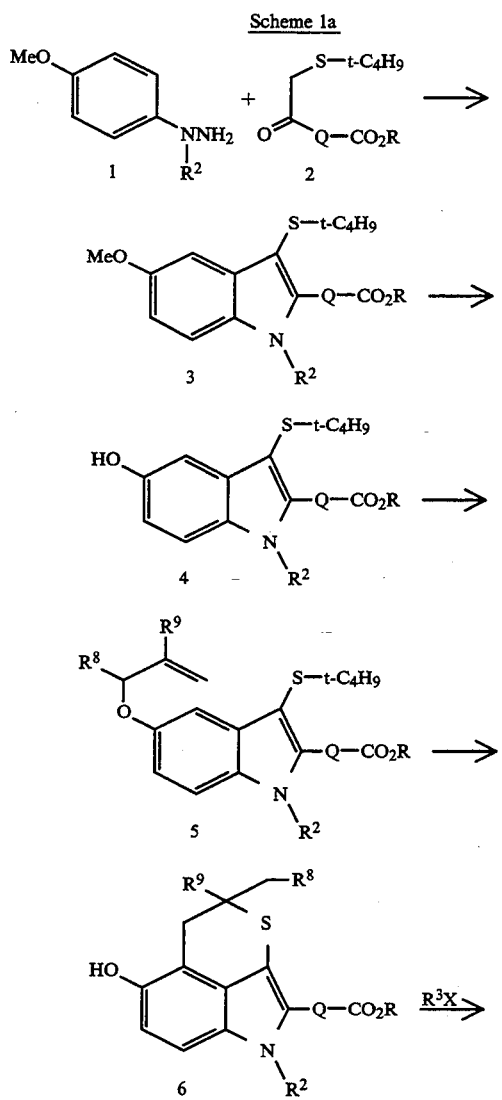

The conversion of 8 to the compounds of the invention is shown in Scheme 1b. Reaction of 8 with N-hydroxyphthalimide under standard Mitsunobu reaction conditions (Ph$_3$P, DIAD) provides the N-phthaloyl intermediate which is deprotected with hydrazine hydrate to provide O-substituted hydroxylamine intermediate 9. of 9 with R$^4$R$^6$CO wherein R$^4$ and R$^6$ are defined above, in the presence of an acid such as acetic acid provides the desired iminoxy derivative 10. Oxidation of 8 to aldehyde 11 followed by reaction with H$_2$NOR$^6$ provides oxime ether compound 12. N-hydroxyurea 15 is prepared by conversion of 1H to oxime 13, followed by reduction with borane-pyridine complex and treatment of the resulting hydroxylamine 14 with trimethylsilylisocyanate as described in U.S. Pat. No. 5, 095,031.

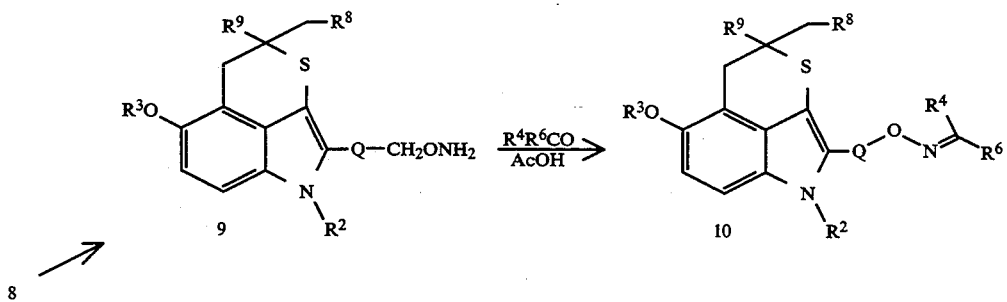

-continued
Scheme 1b

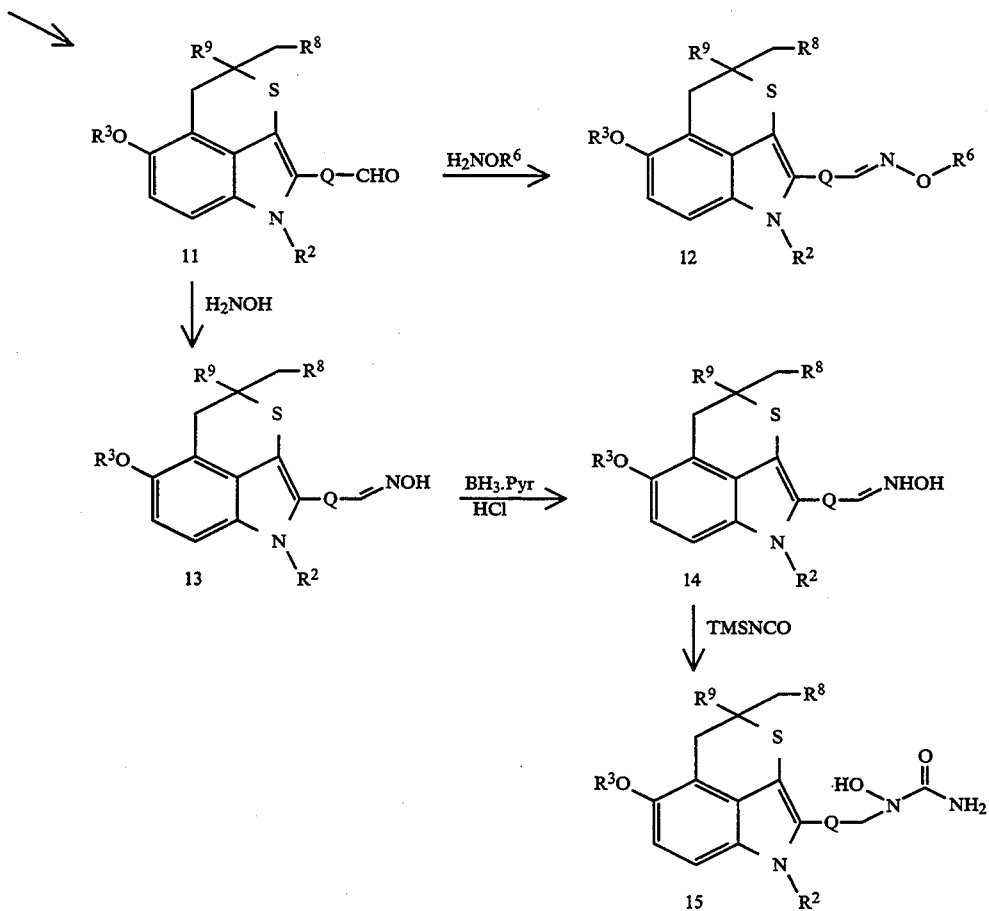

An alternative preparation of the compounds of this invention is outlined in Scheme 2. Indole 16, prepared as described above, is heated in a high boiling solvent such as 1,2-dichlorobenzene in the presence of a mild inorganic base such as sodium acetate to undergo the Claisen rearrangement to provide 4-bromoallyl-5-hydroxyindole 17, which is subsequently treated with a strong base such as sodium hydride, lithium diisopropylamine, n-butyllithium, sodium hexamethyldisilazide, potassium tert-butoxide, or potassium hydride in a polar solvent such as DMF, NMP or THF to provide propargyl intermediate 18. Heating 18 in a high-boiling solvent such as 1,2-dichlorobenzene in the presence of an organic acid such as p-toluenesulfonic acid provides the unsaturated thiopyranoindole 19. Alkylation of 19 with $R_3X$ affords indole 20. Saturated thiopyranoindole 21 is prepared by catalytic hydrogenation of 16 using for example palladium on carbon in an alcoholic solvent. Ester 21 is then converted to the desired compound as described in Schemes 1a and 1b.

Scheme 2

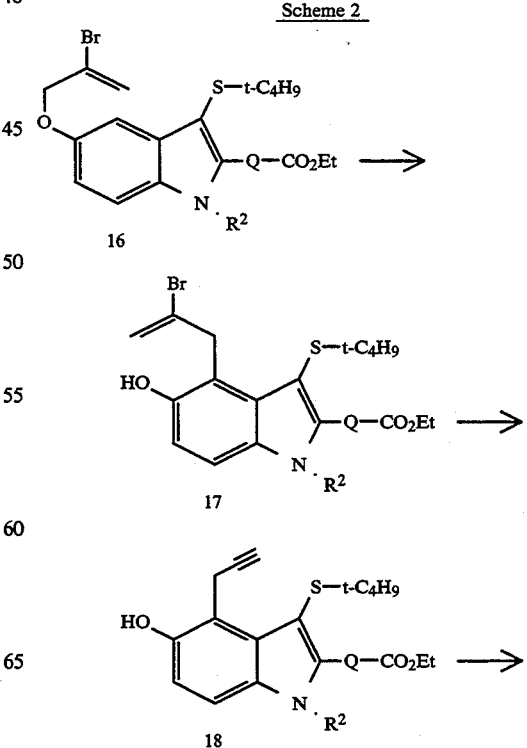

-continued

Scheme 2

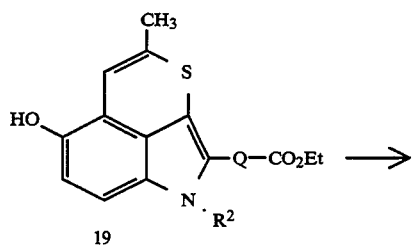
19

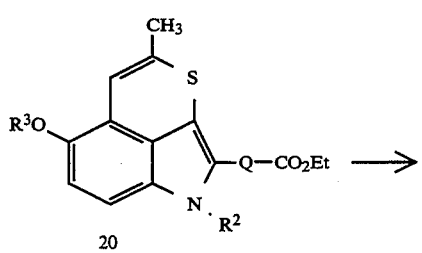
20

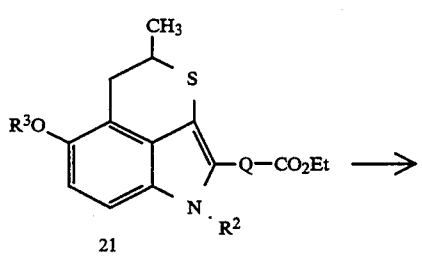
21

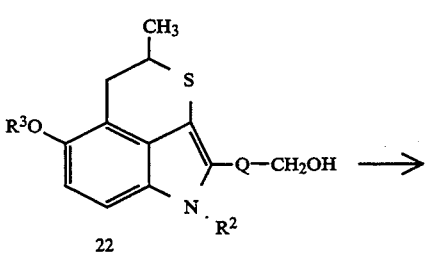
22

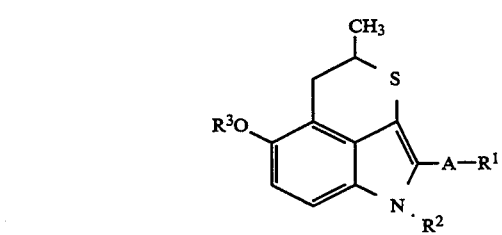

The preparation of compounds in which A is alkoxyalkylene is shown in Scheme 3. Alcohol 8, prepared as described in Scheme 1, is alkylated with a compound of formula X—Q'—CO$_2$R in which Q' is alkylene and R and X are defined above, in the presence of an inorganic base such as sodium hydride, lithium diisopropylamine, butyl lithium, sodium hexamethyldisilazide, potassium tertbutoxide, or potassium hydride to provide alkoxyalkylene compound 23. The ester functionality in 23 is then reduced as described in Scheme 1a, and the resulting alcohol 24 is converted to the desired final compound according to the method of Scheme 1 b.

Scheme 3

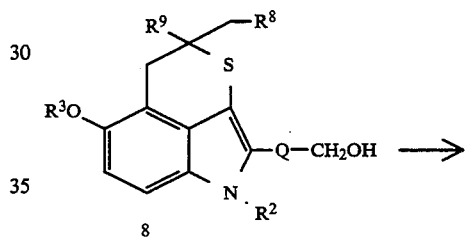
8

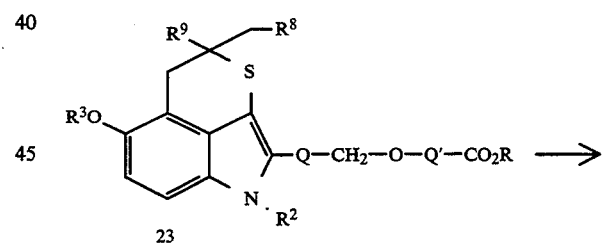
23

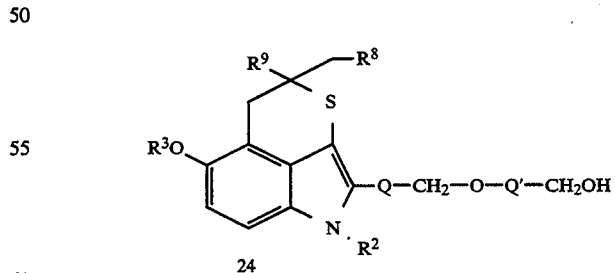
24

The foregoing may be better understood by the following Examples, which are presented for purposes of illustration and are not intended to limit the scope of the invention.

EXAMPLE 1

Preparation of 3-[1-(4-chlorophenyl)-4-methyl-6-(quinolin-2-ylmethoxyl-4,5-dihydro-1H-thiopyrano[2,3,4-c,d]indol-2-yl]-2,2-dimethylpropionaldehyde oxime-O-acetic acid

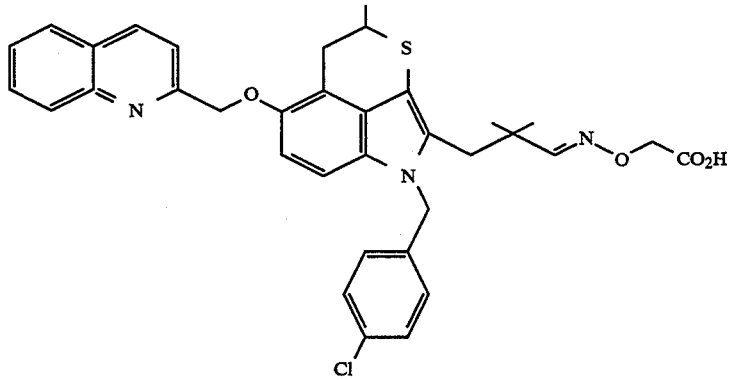

Step 1: 1-(4-chlorobenzyl)-1-(4-methoxyphenyl)hydrazine

To a suspension of 4-methoxyphenylhydrazine hydrochloride (41 g, 230 mmol) in methylene chloride (1000 ml) under nitrogen were added diisopropylamine (79.8 g, 612 mmol), 4-chlorobenzylchloride (40.25 g, 250 mmol) and tetrabutylammonium bromide (22.8 g, 70 mmol). The resulting mixture was stirred at ambient temperature for 48 hours. The reaction mixture was then washed with water, and brine, dried over $MgSO_4$, filtered, and concentrated in vacuo. The residue was purified by column chromatography (silica gel, 2.5% methanol in methylene chloride) followed by washing of the solid with 10% ethyl ether in hexane and drying in vacuo to provide 43.5 g of 1-(4-chlorobenzyl)-1-(4methoxyphenyl)hydrazine, mp. 55° C.

Step 2: ethyl 3-(1-(4-chlorobenzyl)-3-(1,1-dimethylethylthio)-5-methoxyindol-2-yl)-2,2-dimethylpropionate A solution of 1-(4-chlorobenzyl)-1-(4-methoxyphenyl)hydrazine (38.25 g, 150 mmol), prepared as in step 1, in toluene (250 ml) was treated with acetic acid (175 ml) and ethyl 5-t-butylthio-2,2-dimethyl-4-oxopentanoate (38.2 g, 150 mmol) and the resulting mixture was stirred in the dark at ambient temperature for 4 days. The reaction mixture was diluted with water, the organic layer was washed with water, and brine, dried over $MgSO_4$, filtered, and concentrated under reduced pressure. The residue was purified by column chromatography (silica gel, hexane-ethyl acetate 4:1 ) to provide 36.5 g of ethyl 3-(1-(4-chlorobenzyl)-3-(1,1-dimethylethylthio)-5-methoxyindol-2-yl)-2,2-dimethyl propionate.

Step 3: ethyl 3-(1-(4-chlorobenzyl)3-(1,1-dimethylethylthio)-5-hydroxyindol-2-yl)-2,2-dimethylpropionate To a suspension of aluminum chloride (26.3 g, 198 mmol) in t-butylthiol (60 ml) at 0° C. was added a solution of 3-(1-(4-chlorobenzyl)-3-(1,1-dimethylethylthio)-5-methoxyindol-2-yl)-2,2-dimethylpropionate (32 g, 66 mmol), prepared as in step 2, in methylene chloride (90 ml) and the reaction mixture was stirred at 0° C. for 10 min and at ambient temperature for 3 hours. The mixture was then poured into ice and acidified with 10% HCl, the organic layer was washed with water, and brine, dried over $MgSO_4$, filtered, and concentrated in vacuo to provide a white solid. The solid was washed with 20% solution of ethyl ether in hexane, and dried in vacuo to as afford 21.8 g of ethyl 3-(1-(4-chlorobenzyl)-3-(t-butylthio)-5-hydroxyindol-2-yl)-2,2-dimethylpropionate.

Step 4: ethyl 3-(1-(4-chlorobenzyl)-3-(1,1-dimethylethylthio)-5-allyloxyindol-2-yl)-2,2-dimethyltpropionate A mixture of allyl bromide (1.81 g, 15 mmol) potassium carbonate (4.14 g, 30 mmol) and ethyl 3-(1-(4-chlorobenzyl)-3-(t-butylthio)-5-hydroxyindol-2-yl)-2,2dimethylpropionate (7.15 g, 15 mmol), prepared as in step 3, in anhydrous DMF (40 ml) was heated at 60° C for 3 hours, and stirred at ambient temperature for 17 hours. The reaction mixture was diluted with brine and extracted with ethyl acetate. The combined organics were washed with brine, dried over $MgSO_4$, filtered, and concentrated in vacuo to provide a white solid. The solid was triturated with hexane (100 ml), filtered and dried in vacuo dried to obtain 6.65g of ethyl 3-(1-(4-chlorobenzyl)-3-(1,1-dimethylethylthio)-5-allyloxyindol-2-yl)-2,2dimethylpropionate as a white solid.

Step 5. ethyl 3-[1-(4-chlorobenzyl)-4-methyl-6-hydroxy]-4,5-dihydro-1H-thiopyrano[2,3,4-c,d]indol-2-yl]-2,2-dimethylpropionate A suspension of ethyl 3-(1-(4-chlorobenzyl)-3-(1,1-dimethylethylthio)-5-allyloxyindol-2-yl)-2,2-dimethylpropionate (6.4 g, 12.5 mmol), prepared as in step 4, and catalytic p-toluenesulfonic acid in 1,2,dichlorobenzene (40 ml), was heated at 180 ° C. under $N_2$ for 18 hours. The reaction mixture was cooled to ambient temperature and concentrated. The residue was purified by chromatography on silica gel (hexane:ethyl acetate, 4:1 ) to obtain 3.2 g of ethyl 3-[1-(4-chlorobenzyl)-4-methyl-6-hydroxy]-4,5-dihydro-1H-thiopyrano[2,3,4-c,d]indol-2-yl]-2,2dimethylpropi as beige colored solid.

Step 6: ethyl 3-[1-(4-chlorobenzyl)-4-methyl-6-(quinolin-2-ylmethoxyl-4,5-dihydro-1H-thiopyrano[2.3.4-c,d]indol-2-yl]-2,2-dimethylpropionate A mixture of chloromethylquinoline hydrochloride (0.9 g, 4.0 mmol), potassium carbonate (1.7 g, 12 mmol) and ethyl 3-[1-(4-chlorobenzyl)-4-methyl-6-hydroxy]-4,5-dihydro-1H-thiopyrano[2,3,4-c,d]indol-2-yl]-2,2-dimethylpropionate (2.37 g, 5 mmol), prepared as in step 5, in anhydrous DMF (30 ml) was heated at 60° C. for 3 hours and stirred at ambient temperature for 15 hours. The reaction mixture was poured into water and extracted with ethyl acetate (80 ml). The organic layer was washed with brine, dried over $MgSO_4$, filtered, and concentrated in vacuo to provide 1.8 g of ethyl 3-[1-(4-chlorobenzyl)-4-methyl-6-(quinolin-2-ylmethoxy)-4,5-dihydro-1H-thiopyrano[2,3,4-c,d]indol-2-yl]-2,2-dimethylpropionate.

Step 7: 3-[1-(4-chlorobenzyl)-4-methyl-6-(quinolin-2-ylmethoxyl-4,5-dihydro-1H-thiopyrano[2,3,4-c,d]indol-2-yl]-2,2-dimethylpropanol To a solution of ethyl 3-[1-(4-chlorobenzyl)-4-methyl-6-(quinolin-2-ylmethoxy]-4,5-dihydro-1H-thiopyrano[2,3,4-c,d]indol-2-yl]-2,2dimethylpropionate (1.2 g, 2 mmol), prepared as in step 6, in ethanol (30 ml) and THF (20 ml) were added under $N_2$ powdered calcium chloride (0.45 g, 4 mmol) and sodium borohydride (0.3 g, 8 mmol) and the resulting mixture was stirred at 0° C. for 2 hours and at ambient temperature for 14 hours. The reaction mixture was neutralized with 6N HCl and extracted with ethyl acetate. The extract was washed with water, and brine, dried over $MgSO_4$, filtered, and concentrated in vacuo to provide 0.9 g of 3-[1-(4-chlorobenzyl)-4-methyl-6-(quinolin-2-ylmethoxy]-4,5-dihydro-1H-thiopyrano[2,3,4-c,d]indol-2-yl]-2,2-dimethylpropanol.

Step 8: 3-[1-(4-chlorobenzyl)-4-methyl-6-(quinolin-2-ylmethoxyl-4,5-dihydro-1H-thiopyrano[2,3,4-c,d]indol-2-yl]-2,2-dimethylpropionaldehyde To a solution of oxalyl chloride (0.26 ml, 2.5 mmol) in $CH_2Cl_2$ (15 ml) at −78° C. under $N_2$ was added slowly dimethyl sulfoxide (0.35 ml, 5 mmol), followed after 5 minutes by 3-[1-(4-chlorobenzyl)-4-methyl-6-(quinolin-2-ylmethoxy]-4,5-dihydro-1H-thiopyrano[2,3,4-c,d]indol-2-yl]-2,2-dimethylpropanol (0.9 g, 1.6 mmol). The reaction mixture was stirred at −78 ° C. for 30 min and then treated with triethylamine (1.4 ml, 10 mmol). The reaction mixture was diluted with $CH_2Cl_2$ and washed with water and brine. The organic layer was dried over $MgSO_4$, filtered, and concentrated in vacuo. The residue was suspended in 10% ethyl ether in hexane, filtered, and dried in vacuo to provide 0.6 g of pure 3-[1-(4-chlorobenzyl)-4-methyl-6-(quinolin-2-ylmethoxy]-4,5-dihydro-1H-thiopyrano[2,3,4-c,d]indol-2-yl]-2,2-dimethylpropionaldehyde.

Step 9: 3-[1-(4-chlorobenzyl)-4-methyl-6-(quinolin-2-ylmethoxyl-4,5-dihydro-1H-thiopyrano[2,3,4-c,d]indol-2-yl]-2,2-dimethylpropionaldehydeoxime-O-acetic acid A mixture of 3-[1-(4-chlorobenzyl)-4-methyl-6-(quinolin-2-ylmethoxy]-4,5-dihydro-1H-thiopyrano[2,3,4-c,d]indol-2-yl]-2,2-dimethylpropionaldehyde (0.6 g, 1:1 mmol), prepared as in step 8, carboxymethoxylamine hydrochloride (150 mg, 0.65 mmol) and sodium acetate trihydrate (85 mg, 0.65 mmol) in methanol (52 ml), as water (25 ml) and THF (20 ml) was stirred at ambient temperature for 3 hours, and then concetrated in vacuo. The residue was purified by chromatography on silica gel (ethyl acetate-hexane acetic acid 80:19:1 ), followed by recrystallization from ethyl acetate-hexane to afford 395 mg of 3-[1-(4-chlorobenzyl)-4-methyl-6-(quinolin-2-ylmethoxy]-4,5-dihydro-1H-thiopyrano[2,3,4-c,d]indol-2-yl]-2,2dimethylpropionaldehyde oxime-O-acetic acid. mp. 188°–190 ° C. 1H NMR (300 MHz, DMSO-d6) δ 1.09 (d, 6H, J=12 Hz), 1.41 (d, 3H, J=7 Hz), 2.73 (m, 4H), 3.42 (m, 1H), 4.44 (s, 2H), 5.33 (m, 4H), 6.89 (m, 3H), 7.06 (d, 1H, J=9 Hz), 7.31 (d, 2H, J=9 Hz), 7.53 (s, 1H), 7.61 (m, 1H), 7.72 (d, 1H, J=9 Hz), 7.78 (m, 1H), 8.0 (m, 2H), 8.42 (d, 1H, J=9 Hz). Ms (DCI/NH3) m/e 628 $(M+H)^+$. Anal. calc'd for $C_{35}H_{34}ClN_3O_4S$: C, 66.91; H, 5.45; N, 6.68. Found: C, 66.86; H, 5.52; N, 6.59.

EXAMPLE 2

Preparation of 3-[1-(4-chlorobenzyl)-4-methyl-6-(5-phenylpyridin-2-ylmethoxy]-4,5-dihydro-1H-thiopyrano[2,3,4-c,d]indol-2-yl]-2,2-dimethylpropionaldehyde oxime-O-acetic acid

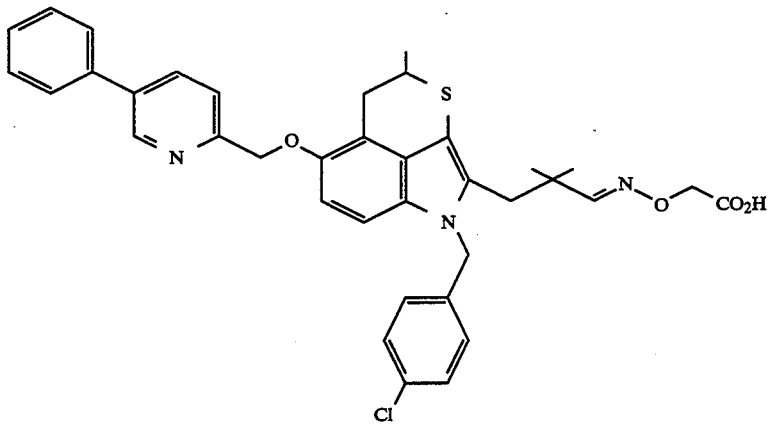

The desired material was prepared according to the procedure of Example 1, except substituting 5-phenyl-2-picolyl chloride, prepared as described in EPA 0 518 426 A1, for chloromethylquinoline hychloride in step 6 above. m.p. 150°–152° C. $^1$H NMR (300 MHz. DMSO-d6) δ 1.08 (d, 6H, J=12 Hz), 1.40 (d, 3H, J=6 Hz), 2.72 (m, 4H), 3.54 (m, 1H), 4.34 (s, 2H), 5.18(m, 2H), 5.35(m, 2H), 6.90 (m, 3H), 7.06 (d, 1H. J=9 Hz), 7.30 (d, 2H, J=9 Hz), 7.44 (m, 1H), 7.51 (m, 3H), 7.63 (d, 1H, J=9 Hz), 7.73 (m, 2H), 8.13 (m, 1H), 8.8 (m, 1H). MS (DCI/NH3) m/e 654 $(M+H)^+$. Anal. Calc'd for $C_{37}H_{36}ClN_3O_4S \cdot H_2O$: C, 66.12, H, 5.59, N. 6.25 Found. C, 65.93 H, 5.41, N. 6.08. The compounds represented in Table 1 are prepared by the method described for Example 1 except substituting the requisite groups for $R_2$ and $R_3$.

TABLE 1

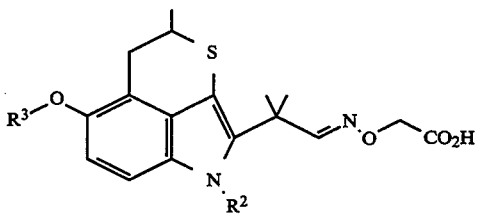

| Example | R² | R³ |
|---|---|---|
| 3 | 4-chlorophenylmethyl | 2-pyridylmethyl |
| 4 | 4-chlorophenylmethyl | 2-thiazolylmethyl |
| 5 | 4-chlorophenylmethyl | 4-thiazolylmethyl |
| 6 | 4-chlorophenylmethyl | 5-thiazolylmethyl |
| 7 | 4-chlorophenylmethyl | 2-pyrazinylmethyl |
| 8 | 4-chlorophenylmethyl | 2-benzothiazolylmethyl |
| 9 | 4-chlorophenylmethyl | 2-pyrimidylmethyl |
| 10 | 4-chlorophenylmethyl | 5-oxazolylmethyl |
| 11 | 4-chlorophenylmethyl | 2-naphthyridinylmethyl |
| 12 | 4-chlorophenylmethyl | 3-isoquinolinylmethyl |
| 13 | 4-chlorophenylmethyl | 6-methoxyquinol-2ylmethyl |
| 14 | 4-chlorophenylmethyl | 4-phenylpyrid-2-ylmethyl |
| 15 | 4-chlorophenylmethyl | 4-(4-chlorophenyl)pyrid-2-ylmethyl |
| 16 | 4-chlorophenylmethyl | 3-(4-chlorophenyl)pyrid-2-ylmethyl |
| 17 | 4-chlorophenylmethyl | 6-chloroquinol-2ylmethyl |
| 18 | 4-chlorophenylmethyl | 2(4-chlorophenyl)thiazol-4ylmethyl |
| 19 | 4-pyridylmethyl | 5-(4-chlorophenyl)pyrid-2-ylmethyl |
| 20 | 4-pyridylmethyl | 5-(4-fluorophenyl)pyrid-2-ylmethyl |
| 21 | 3-pyridylmethyl | 5-(4-chlorophenyl)pyrid-2-ylmethyl |
| 22 | 3-pyridylmethyl | 5-(4-fluorophenyl)pyrid-2-ylmethyl |
| 23 | 2-pyridylmethyl | 5-(4-chlorophenyl)pyrid-2-ylmethyl |
| 24 | 2-pyridylmethyl | 5-(4-fluorophenyl)pyrid-2-ylmethyl |
| 25 | 4-fluorophenylmethyl | 5-(4-chlorophenyl)pyrid-2-ylmethyl |
| 26 | 4-fluorophenylmethyl | 5-(4-fluorophenyl)pyrid-2-ylmethyl |
| 27 | 4-fluorophenylmethyl | 2-pyridylmethyl |
| 28 | 4-fluorophenylmethyl | 2-quinolylmethyl |
| 29 | 4-fluorophenylmethyl | 4-thiazolylmethyl |
| 30 | 4-fluorophenylmethyl | 5-thiazolylmethyl |
| 31 | 4-fluorophenylmethyl | 2-thiazolylmethyl |
| 32 | 4-fluorophenylmethyl | 6-methoxyquinol-2ylmethyl |
| 33 | 4-fluorophenylmethyl | 6-chloroquinol-2ylmethyl |
| 34 | 4-fluorophenylmethyl | 2-benzothiazolylmethyl |
| 35 | 4-phenylphenylmethyl | 2-quinolylmethyl |
| 36 | 4-phenoxyphenylmethyl | 2-quinolylmethyl |
| 37 | 3-phenylphenylmethyl | 2-quinolylmethyl |
| 38 | 3-phenoxyphenylmethyl | 2-quinolylmethyl |
| 39 | 3-(4-chlorophenoxy)phenylmethyl | 2-quinolylmethyl |
| 40 | 4-(4-fluorophenoxy)phenylmethyl | 2-quinolylmethyl |
| 41 | 3-(4-fluorophenoxy)phenylmethyl | 2-quinolylmethyl |
| 42 | 4-(4-chlorophenoxy)phenylmethyl | 2-quinolylmethyl |
| 43 | 3-(pyrid-2-yl)phenylmethyl | 2-quinolylmethyl |
| 44 | 4-(pyrid-2-yl)phenylmethyl | 2-quinolylmethyl |
| 45 | 2-(pyrid-2-yl)phenylmethyl | 2-quinolylmethyl |
| 46 | 2-(pyrid-2-yloxy)phenylmethyl | 2-quinolylmethyl |
| 47 | 3-(pyrid-2-yloxy)phenylmethyl | 2-quinolylmethyl |
| 48 | 4-(pyrid-2-yloxy)phenylmethyl | 2-quinolylmethyl |

The compounds represented in Table 2 are prepared by the method described in Scheme 3.

TABLE 2

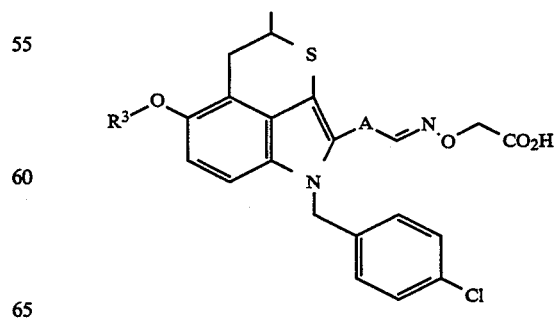

| Example | R₃ | A |
|---|---|---|
| 49 | 2-quinolylmethyl | CH₂OCH₂ |
| 50 | 2-quinolylmethyl | CH₂OCH(Me) |

TABLE 2-continued

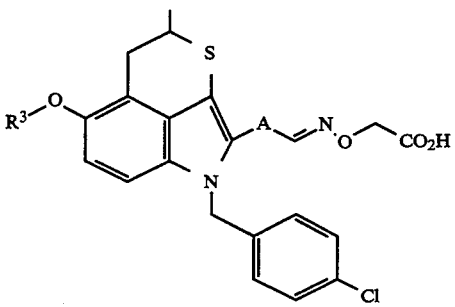

| Example | R3 | A |
|---|---|---|
| 51 | 2-quinolylmethyl | CH$_2$O(CH$_2$)$_2$ |
| 52 | 2-quinoiylmethyl | (CH$_2$)$_2$OCH$_2$ |
| 53 | 2-quinolylmethyl | (CH$_2$)$_2$OCH(Me) |
| 54 | 5-phenylpyrid-2-ylmethyl | CH$_2$OCH$_2$ |
| 55 | 5-phenylpyrid-2-ylmethyl | CH$_2$OCH(Me) |
| 56 | 5-phenylpyrid-2-ylmethyl | CH$_2$O(CH$_2$)$_2$ |
| 57 | 5-phenylpyrid-2-ylmethyl | (CH$_2$)$_2$OCH$_2$ |
| 58 | 5-phenylpyrid-2-ylmethyl | (CH$_2$)$_2$OCH(Me) |

We claim:

1. A compound having the structure

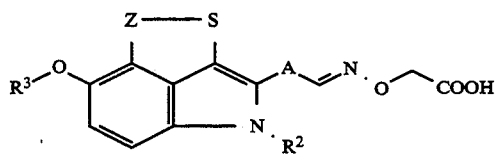

or a pharmaceutically acceptable salt thereof wherein
A is selected from the group consisting of
straight or branched alkylene of one to twelve carbon atoms,
cycloalkylene of three to eight carbon atoms, and
alkoxyalkylene in which the alkyoxy and alkylene portions are independently of one to six carbon atoms;
R$^2$ is selected from the group consisting of
(a) unsubstituted phenylalkyl in which the alkyl portion is of one to six carbon atoms, and
(b) phenylalkyl substituted with one to three substituents selected from the group consisting of
alkyl of one to six carbon atoms,
haloalkyl of one to six carbon atoms,
alkoxy of one to six carbon atoms, and
halogen, and
(c) pyridylalkyl wherein the alkyl portion is of one to six carbon atoms;
R$^3$ is selected from the group consisting of
(a) optionally substituted pyridylalkyl or quinolylallcyl wherein the alkyl portion is of one to six carbon atoms and the optional substituents are selected from the group consisting of
alkyl of one to six carbon atoms,
alkoxy of one to six carbon atoms,
haloalkyl of one to six carbon atoms,
halogen, and
unsubstituted phenyl, and
phenyl substituted with a substituent selected from the group consisting of alkyl of one to six carbon atoms, and
halogen; and Z is selected from the group consisting of alkylene of one to four carbon atoms and alkenylene of one to four carbon atoms;
with the proviso that R$^2$ may be pyridylalkyl only when R$^3$ is quinolylalkyl.

2. A compound or pharmaceutically acceptable salt thereof as defined by claim 1 selected from the group consisting of
3-[1-(4-chlorobenzyl )-4-methyl-6-(quinolin-2-ylmethoxy)-4,5-dihydro-1H-thiopyrano[2,3,4-c,d]indol-2-yl]-2,2-dimethylpropionaldehyde oxime-O-acetic acid,
3-[1-(4-chlorobenzyl)-4-methyl-6-(5-phenylpyridin-2-ylmethoxy)-4,5-dihydro-1H-thiopyrano[2,3,4-c,d]indol-2-yl]-2,2-dimethylpropionaldehyde oxime-O-acetic acid,
3-[1-(4-chlorobenzyl)-4-methyl-6-(pyrid-2-ylmethoxy)-4,5-dihydro-1H-thiopyrano[2,3,4-c,d]indol-2-yl]-2,2-dimethylpropionaldehyde oxime-O-acetic acid,
3-[1-(4-chlorobenzyl)-4-methyl-6-(6-methoxyquinolin-2-ylmethoxy)-4,5-dihydro-1H-thiopyrano[2,3,4-c,d]indol-2-yl ]-2,2-dimethylpropionaldehyde oxime-O-acetic acid,
3-[1-(4-chlorobenzyl)-4-methyl-6-(6-chloroquinolin-2-ylmethoxy)-4,5-dihydro-1H-thiopyrano[2,3,4-c,d]indol-2-yl]-2,2-dimethylpropionaldehyde oxime-O-acetic acid,
3-[1-(4-fluorobenzyl)-4-methyl-6-(quinolin-2-ylmethoxy)-4,5-dihydro-1H-thiopyrano[2,3,4-c,d]indol-2-yl]-2,2-dimethylpropionaldehyde oxime-O-acetic acid,
3-[1-(4-fluorobenzyl)-4-methyl-6-(5-phenylpyridin-2-ylmethoxy)4,5-dihydro-1H-thiopyrano[2,3,4-c,d]indol-2-yl ]-2,2-dimethylpropionaldehyde oxime-O-acetic acid,
3-[1-(4-phenoxyphenylmethyl)-4-methyl-6-(quinolin-2-ylmethoxy)-4,5-dihydro-1H-thiopyrano[2,3,4-c,d]indol-2-yl]-2,2-dimethylpropionaldehyde oxime-O-acetic acid,
3-[1-(4-(4-fluorophenoxy)phenylmethyl)-4-methyl-6-(quinolin-2-ylmethoxy)-4,5-dihydro-1H-thiopyrano[2,3,4-c,d]indol-2-yl]-2,2-dimethylpropionaldehyde oxime-O-acetic acid,
3-[1-(4-(pyrid-2-yl)phenylmethyl)-4-methyl-6-(quinolin-2-ylmethoxy)-4,5-dihydro1H-thiopyrano[2,3,4-c,d]indol-2-yl ]-2,2-dimethylpropionaldehyde oxime-O-acetic acid,
[1-(4-chlorobenzyl)-4-methyl-6-(quinolin-2-ylmethoxy)-4,5-dihydro-1H-thiopyrano[2,3,4-c,d]indol-2-ylmethoxy]acetaldehyde oxime-O-acetic acid,
3-1-(4-chlorobenzyl)-4-methyl-6-(quinolin-2-ylmethoxy)-4,5-dihydro-1H-thiopyrano[2,3,4-c,d]indol-2-ylmethoxy]propionaldehyde oxime-O-acetic acid,
[1-(4-chlorobenzyl)-4-methyl-6-(5-phenylpyridin-2-ylmethoxy)-4,5-dihydro-1H-thiopyrano[2,3,4-c,d]indol-2-ylmethoxy]acetaldehyde oxime-O-acetic acid, and
3-[1-(4-chlorobenzyl)-4-methyl-6-(5-phenylpyridin-2-yl methoxy)-4,5-dihydro-1H-thiopyrano[2,3,4-c,d]indol-2-ylmethoxy]propionaldehyde oxime-O-acetic acid.

3. A compound or pharmaceutically acceptable salt thereof as defined by claim 1 selected from
3-[1-(4-chlorophenyl)-4-methyl-6-(quinolin-2-ylmethoxy)-4,5-dihydro-1H-thiopyrano[2,3,4-c,d]indol-2-yl]-2,2-dimethylpropionaldehyde oxime-O-acetic acid, and
3-[1-(4-chlorobenzyl)-4-methyl-6-(5-phenylpyridin-2-ylmethoxy]-4,5-dihydro-1H-thiopyrano[2,3,4-c,d]indol-2-yl]-2,2-dimethylpropionaldehyde oxime-O-acetic acid.

4. A pharmaceutical composition for inhibiting the biosynthesis of leukotrienes comprising a therapeutically effective amount of a compound as defined by claim 1 in combination with a pharmaceutically acceptable carrier.

5. A method of inhibiting the biosynthesis of leukotrienes comprising administering to a mammal in need of such treatment a therapeutically effective amount of a compound as defined by claim 1.

* * * * *